US 9,185,897 B2

(12) United States Patent
Boyd et al.

(10) Patent No.: US 9,185,897 B2
(45) Date of Patent: Nov. 17, 2015

(54) METHODS TO DELIVER AND MAINTAIN VOLATILE COMPOUNDS

(71) Applicant: AUBURN UNIVERSITY, Auburn, AL (US)

(72) Inventors: Maurice M. Boyd, Oakland, FL (US); Ronald D. Neuman, Auburn, AL (US); Andrew B. Shelton, Auburn, AL (US); Wiley M. Cauthen, Winter Garden, FL (US); Ralph H. Zee, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 0 days.

(21) Appl. No.: 14/195,048

(22) Filed: Mar. 3, 2014

(65) Prior Publication Data
US 2014/0173971 A1    Jun. 26, 2014

Related U.S. Application Data

(63) Continuation-in-part of application No. 13/803,260, filed on Mar. 14, 2013, which is a continuation-in-part of application No. 13/300,067, filed on Nov. 18, 2011.

(60) Provisional application No. 61/415,035, filed on Nov. 18, 2010.

(51) Int. Cl.
*A01M 13/00*    (2006.01)
*A01M 1/20*    (2006.01)
(Continued)

(52) U.S. Cl.
CPC .............. *A01M 13/00* (2013.01); *A01M 1/2044* (2013.01); *A01M 1/2055* (2013.01); *A01M 1/245* (2013.01);
(Continued)

(58) Field of Classification Search
CPC ... A01M 13/00; A01M 1/2044; A01M 29/12; A01M 1/02; A01M 1/2055; A01M 13/003; A01M 1/245; A61D 7/00; A61D 7/04; A01N 25/34; A01N 25/00
USPC ................. 43/132.1, 124, 125, 126, 129, 900

IPC ..................................... A01M 13/00,7/00, 1/20
See application file for complete search history.

(56) References Cited

U.S. PATENT DOCUMENTS

| 276,844 A | 5/1883 | Manahan |
| 1,991,851 A | 2/1935 | Hammell |

(Continued)

FOREIGN PATENT DOCUMENTS

| DE | 2832248 A1 | 1/1980 |
| DE | 2945655 A1 | 5/1981 |

(Continued)

OTHER PUBLICATIONS

Agrawal et al., Induced Plant Defenses Against Pathogens and Herbivores, Biochemistry, Ecology, and Agriculture, APS Press, St. Paul, 1999.

(Continued)

*Primary Examiner* — Lisa Tsang
(74) *Attorney, Agent, or Firm* — Gardner Groff Greenwald & Villanueva, PC (57) ABSTRACT

Methods to create and maintain pre-designed geometrically shaped volumes of an effective dynamic mixture of volatile compounds encompassing an object of protection for very long times, up to one or more years, for control of pests and pest-borne diseases in open outdoor environments of importance to humans, animals and plants. The methods include using a plurality of passive flow control nozzles containing mass-regulating barriers with retaining fixtures, strategically positioned and uniquely oriented, connected to volatile compound-storing structures with replenishing connectors, for delivering controlled release of volatile compounds using individual passive flow control nozzles that dispense volatile compounds at continuous, predetermined, substantially constant and sustainable release rates over extended periods of time, appurtenances to protect the mass-regulating barriers while in operation, and sensors to monitor the biologically active threshold and the concentrations of volatile compound within the pre-designed geometrically shaped volumes of volatile compounds.

21 Claims, 6 Drawing Sheets

(51) Int. Cl.
*A01N 25/00* (2006.01)
*A01M 29/12* (2011.01)
*A01N 25/34* (2006.01)
*A01M 1/24* (2006.01)
*A61D 7/04* (2006.01)

(52) U.S. Cl.
CPC ............. *A01M 13/003* (2013.01); *A01M 29/12* (2013.01); *A01N 25/00* (2013.01); *A01N 25/34* (2013.01); *A61D 7/04* (2013.01)

(56) References Cited

U.S. PATENT DOCUMENTS

| | | | |
|---|---|---|---|
| 2,412,326 | A | 12/1946 | Dupuy |
| 3,204,871 | A | 9/1965 | Callander |
| 3,412,935 | A | 11/1968 | O'Keeffe |
| 3,856,204 | A | 12/1974 | Chand |
| 4,195,058 | A | 3/1980 | Patel |
| 4,356,969 | A | 11/1982 | Obermayer et al. |
| 4,526,320 | A | 7/1985 | Von Philipp et al. |
| 4,538,377 | A | 9/1985 | Thornton |
| 4,600,146 | A | 7/1986 | Ohno |
| 4,666,767 | A | 5/1987 | Von Kohorn et al. |
| RE32,513 | E | 10/1987 | Seaber et al. |
| 4,734,281 | A | 3/1988 | Yamamoto et al. |
| 4,753,389 | A | 6/1988 | Davis |
| 4,923,119 | A | 5/1990 | Yamamoto et al. |
| 5,063,706 | A | 11/1991 | Aki et al. |
| 5,109,629 | A * | 5/1992 | King et al. .............. 43/132.1 |
| 5,317,831 | A | 6/1994 | Fletscher |
| 5,394,643 | A * | 3/1995 | Schmittmann ............. 43/124 |
| 5,497,942 | A | 3/1996 | Zingle et al. |
| 5,765,751 | A | 6/1998 | Joshi |
| 5,829,188 | A * | 11/1998 | Tanitomi ............ A01M 1/2044 261/24 |
| 6,199,770 | B1 | 3/2001 | King et al. |
| 6,219,960 | B1 * | 4/2001 | Contadini et al. ............. 43/121 |
| 6,243,986 | B1 | 6/2001 | Crowley |
| 6,298,596 | B1 * | 10/2001 | Pratizzoli ..................... 43/129 |
| 6,352,721 | B1 | 3/2002 | Faour |
| 6,362,235 | B1 | 3/2002 | Nolen et al. |
| 6,582,714 | B1 | 6/2003 | Emmrich et al. |
| 6,820,773 | B1 | 11/2004 | Orth |
| 6,877,272 | B2 | 4/2005 | Hoshall |
| 6,977,088 | B2 | 12/2005 | Munzel et al. |
| 7,032,346 | B1 | 4/2006 | Richard |
| 7,213,770 | B2 | 5/2007 | Martens, III et al. |
| 7,295,898 | B2 | 11/2007 | Lovett et al. |
| 7,451,568 | B2 | 11/2008 | Hoshall |
| 7,481,380 | B2 | 1/2009 | Kvietok et al. |
| 7,614,568 | B2 | 11/2009 | Joshi et al. |
| 8,657,254 | B2 | 2/2014 | Cate et al. |
| 2004/0050951 | A1 | 3/2004 | Almero |
| 2005/0129568 | A1 | 6/2005 | Kubby et al. |
| 2006/0186220 | A1 | 8/2006 | Kubby et al. |
| 2006/0261188 | A1 * | 11/2006 | Ito ......................... A01M 1/02 239/306 |
| 2007/0084105 | A1 * | 4/2007 | Lindsay ............. A01M 1/2094 43/129 |
| 2007/0245937 | A1 * | 10/2007 | Allan et al. ................... 111/127 |
| 2008/0191050 | A1 | 8/2008 | Blondeau et al. |
| 2010/0024280 | A1 * | 2/2010 | Reed et al. .................. 43/132.1 |
| 2011/0252694 | A1 * | 10/2011 | Poss et al. ..................... 43/125 |

FOREIGN PATENT DOCUMENTS

| | | |
|---|---|---|
| WO | 9828161 A1 | 7/1998 |
| WO | 03086490 A1 | 10/2003 |

OTHER PUBLICATIONS

Auger et al.; Leek Odor Analysis by Gas Chromatography and Identification of the Most Active Substance for the Leek Moth, Acrolepiopsis Assectella; Journal of Chemical Ecology, vol. 15, No. 6; 1989 Plenum Publishing Corporation; pp. 1847-1854.

Beattie et al.; Australia and Huanglongbing.

Dugravot et al.; Dimethyl Disulfide Exerts Insecticidal Neurotoxicity Through Mitochondrial Dysfunction and Activation of Insect K ATP Channels; J Neurophysiol 90:259-270; 2003 The American Physiological Society.

Halbert et al.; Asian Citrus Psyllids (Sternorrhyncha: Psyllidae) and Greening Disease of Citrus: A Literature Review and Assessment of Risk in Florida; Florida Entomol. 87(3); pp. 330-353; 2004.

Huang et al.; Bioactivities of Methyl Allyl Disulfide and Diallyl Trisulfide From Essential Oil of Garlic to Two Species of Stored-Product Pests, Sitophilus Zeamais (Coleoptera: Curculionidae) and Tribolium Castaneum (Coleoptera: Tenebrionidae); J. Econ. Entomol. 93(2): 537-543 (2000) Entomological Society of America.

International Search Report and Written Opinion of PCT/US2011/061441; Jun. 1, 2012; 23 pgs.

Invitation to Pay Additional Fees for PCT/US2011/061441; Mar. 26, 2012; 5 pgs.

James, David G.; Field Evaluation of Herbivore-Induced Plant Volatiles as Attractants for Beneficial Insects: Methyl Salicylate and the Green Lacewing, Chrysopa Nigricornis; Journal of Chemical Ecology, vol. 29, No. 7; Jul. 2003 Plenum Publishing Corporation; pp. 1601-1609.

Karl et al.; Chemical Sensing of Plant Stress at the Ecosystem Scale; Biogeosciences, 5, 1287-1294, 2008; Copernicus Publications on behalf of the European Geosciences Union.

Maia et al.; Plant-Based Insect Repellents: A Review of Their Efficacy, Development and Testing; Malara Journal 10 (Suppl 1); pp. 511-525; 2011.

Miles et al.; Evidence that Cell Death is Associated with Zebra Chip Disease in Potato Tubers; Am. J. Pt Res (2010) 87:337-349; Potato Association of America 2010.

Onagbola et al.; Guava Leaf Volatiles and Dimethyl Disulphide Inhibit Response of Diaphorina Citri Kuwayama to Host Plant Volatiles; J. Appl. Entomol. 135; pp. 404-414; 2011.

Stelinski et al.; Update on Development of a Repellent for Asian Citrus Psyllid; University of Florida, IFAS; Oct./Nov.2009; pp. 3-4.

Strickman, Daniel; Area Repellent Products; CRC Press; Boca Raton; pp. 385-393; 2007.

Zaka et al.; Repellent Effect of Guava Leaf Volatiles on Settlement of Adults of Citrus Psylla, Diaphorina Citri Kuwayama, on Citrus; Insect Science (2010) 17, 39-45.

* cited by examiner

METHODS TO DELIVER AND MAINTAIN VOLATILE COMPOUNDS

CROSS-REFERENCE TO RELATED APPLICATIONS

This application is a continuation-in-part of U.S. Non-Provisional patent application Ser. No. 13/803,260, filed Mar. 14, 2013, now pending, which claims the benefit of U.S. Non-Provisional patent application No. 13/300,067, filed Nov. 18, 2011, now pending, which claims the benefit of U.S. Provisional Patent Application Ser. No. 61/415,035 filed Nov. 18, 2010, all of which are incorporated herein by reference in their entireties.

TECHNICAL FIELD

The present invention relates generally to methods for controlled delivery of volatile compounds, and more particularly to establishing and maintaining pre-designed geometrically shaped volumes of an effective dynamic mixture of volatile compounds that encompass and protect an object (human, animal or plant) from pests and pest-borne diseases in open outdoor environments over very long time periods, such as up to and exceeding one year.

BACKGROUND

The term "vector-borne diseases" is commonly used to describe diseases transmitted from an infected host to humans and animals by blood-feeding arthropods. Vectors of human diseases are typically species of blood-feeding mosquitoes and ticks that are able to transmit pathogens (viruses, bacteria or parasites) to humans and other warm-blooded hosts. Malaria, dengue fever, yellow fever and West Nile virus are among the most deadly infectious vector-borne diseases. The number of disease epidemics has dramatically increased in recent years not only in vector-borne human diseases, but also in vector-borne plant diseases.

The control of mosquitoes and other insect vectors of human, animal and plant pathogens is critical to solving various public health and economic problems. Although there have been decades of mosquito control efforts worldwide, mosquito-borne disease epidemics are still prone for resurgence. Mosquito control methods have included chemical (insecticides) and biological (bacteria) techniques, habitat modification, integrated mosquito management and personal protection. One important method of reducing the risk of disease is through the use of repellents to protect people from being fed upon by arthropods. Repellents can be used as either topical repellents or spatial repellents.

Spatial repellents can be defined as repellents which are dispensed into the atmosphere of a three dimensional space and inhibit the ability of mosquitoes to locate and track a target such as humans or livestock (Nolen et al, U.S. Pat. No. 6,362,235). There has been much interest in recent years on using natural plant volatiles as repellents instead of synthetic repellents (Maia and Moore, 2011). However, from a practical application point of view, although there are devices in the marketplace to dispense such repellents, there are limitations to their effectiveness (Strickman, 2007. There are unrealized needs to provide mosquito and blood-feeding arthropod protection to humans and animals over much larger areas in open environments than possible at the present time.

As an example of a vector-borne plant disease, Huanglongbing (HLB) or citrus greening disease is a serious threat to production of citrus crops. The Asian citrus psyllid, *Diaphorina citri* Kuwayama (*D. citri*), is the primary vector in citrus of the bacteria *Candidatus liberibacter asiaticus* and *Candidatus liberibacter americanus*. These bacteria are presumed to be responsible for HLB disease. The range of *D. citri* has expanded into citrus production areas throughout the world, threatening entire citrus groves on a regional scale, thereby making HLB one of the most serious threats to production of citrus worldwide (Halbert and Manjunath, 2004).

Control of the Asian citrus psyllid is critical to the citrus industry. Current efforts to control *D. citri* populations primarily rely on application of broad-spectrum insecticides by area-wide aerial spraying programs. However, numerous applications of pesticides, often eight to ten times annually in Florida, cannot be indefinitely sustained. There are serious issues with *D. citri* developing pesticide resistance, the build-up of environment contaminants, the unintended elimination of natural biological control agents, and pesticide residues in citrus products.

The HLB situation is a crisis and urgently requires new tools to control the *D. citri*. population. Fortunately, there are potential attractive alternatives such as spatial repellents based on plant volatiles or plant-derived essential oils. Although there has been some progress on repellent research in scientific laboratories, a practical repellent system (that includes both repellent and a delivery system) has not yet been developed. One key bottleneck in moving this research forward has been the lack of a slow-release device that maintains the volatile repellent above a behaviorally active threshold for extended periods of time as long as 150-200 days (Onagbola et al., 2011).

The art of emitting or releasing volatile compounds and substances has a long history. There are a variety of devices or systems described in the patent literature to evaporate or dispense volatile compounds or compositions into the atmosphere Emmrich et al., U.S. Pat. No. 6,582,714; Kvietok, et al., U.S. Pat. No. 7,481,380). Materials commonly delivered include fragrances, deodorizers, disinfectants, insecticides, air fresheners, etc. Delivery dispensers typically can be categorized as "active dispensers" or "passive dispensers". For example, a common active dispensing device is the aerosol spray dispenser that propels minute droplets of a volatile composition into the air. Active dispensers include various types of sprayers that operate by pressure, air displacement, or pump action. There are other dispensers that require an energy source. For example, devices or articles that dispense insecticide vapors often utilize the heating or burning of a liquid or solid substance to evaporate the active ingredients. Other dispensing methods include substrates such as paperboard or fabrics impregnated with volatile active ingredients, gelatinous materials that as they dry and shrink release a volatile compound into the air, and micro-encapsulated substances that achieve a slow release of volatile active ingredients. Evaporative surface (non-aerosol) devices typically utilize a wick or porous surface that provides a large surface area from which volatile liquid material can more quickly evaporate passively into the air. Attempts at improvements on the shortcomings of dispensing devices have included combining elements of both active and passive dispensers into a combined device.

Some vapor (or gas) dispensing devices have employed permeation membranes, but their intended usage generally has been focused on more specialized applications. For example, permeable membranes have been used in the production of calibration samples for gas or liquid analyzers, such as in tube devices (O'Keeffe, U.S. Pat. No. 3,412,935) and in devices having improved membrane permeability characteristics (Chand, U.S. Pat. No. 3,856,204). An apparatus used for the treatment of honeybee colonies for different honeybee diseases employed microporous membranes (Orth, U.S. Pat. No. 6,820,773). Vapor-permeable membranes also have found use in a fragrance product (Obermayer and Nichols, U.S. Pat. No. 4,356,969) and in a time-temperature indicator for monitoring the shelf lives of perishable articles (Patel, U.S. Pat. No. 4,195,058).

In an application for pest control, a sex pheromone has been dispensed by using a plastic bag through which the pheromone compound permeated the bag walls and was released as a vapor to the atmosphere (Kauth and Darskus, German Pat. No. 28 32 248; Kauth et al., German Pat. No. 29 45 655). Another approach to the control of a pest employed a capillary tubing of a polymeric material filled with a vaporizable substance, such as a pesticide, fungicide or sex pheromone, which permeated the tube walls and was released to the atmosphere; this dispensing body had good shape-retainability by integrating side-by-side a metal wire with the capillary tubing (Ohno, U.S. Pat. No. 4,600,146). A method for simultaneously controlling the rates of concurrent vapor release of two specific classes of sex pheromone compounds involved mixing in a unique proportion to achieve an overall solubility parameter and enclosing the liquid mixture in a permeable container such that two pheromone compounds permeated the wall and were dispensed into the atmosphere as a vapor (Yamamoto et al., U.S. Pat. No. 4,734,281).

The previously available methods, devices and systems were often limited to dispensing vapors within defined spaces, for example, a room or the area in the immediate vicinity of a device. These vapor dispensers are generally known in the art to provide inadequate effectiveness in larger, more open spaces, especially in large volumes of moving air, most particularly in the case of outdoor environments. Another difficulty is that they are not able to effectively dispense volatile compounds at a sustainable rate over very long periods of time. Furthermore, another undesirable characteristic is that there is often an initial burst of vapor followed by a continuous intensity decline, rather than a delivery of vapor at a rate substantially constant with time.

Additionally, there are commercial mosquito repellent devices utilizing spatial repellents that are marketed to provide protection in outdoor environments. A typical area of coverage is about 200-300 sq ft, but the protection claimed lasts for only about 4-18 hours. Such devices cannot be employed in applications for open environments such as young plantings in citrus groves and protecting humans in large outdoor facilities. These devices are not cost effective since the frequent replacement of repellent is too costly and too labor intensive.

Thus, there clearly is a need for effective methods and systems for the controlled delivery and continuous maintenance of volatile compounds in very large open areas such as agricultural fields, citrus groves, orchards and structures such as large patios or decks and pavilions. However, there are serious challenges in the practical, effective deployment of volatile compounds in open environments. It is relatively simple to release volatile compounds. The current failure is maintaining an effective dynamic mixture of volatile compounds encompassing the object of protection for very long times. Therefore the design goals should include: (1) providing protection of objects of various geometrical shapes with specific spatial extent, (2) establishing effective concentrations under open outdoor conditions for defined volumes of volatile compounds, (3) maintaining the effective dynamic mixture in specific geometrically shaped volumes for very long periods of time, (4) providing continuous, predetermined and substantially constant release rates of volatile compounds from multiple sources, (5) sustaining release rates over extended time periods of protection up to and exceeding one year, (6) fine-tuning or adjusting release rates in the field as needed, and (7) developing methods and systems that employ effective concepts to reduce waste and environmental impact.

The present invention meets these goals for the delivery of volatile compounds in a wide variety of practical applications. As one example, the present invention holds great promise to make available low-cost, highly effective mosquito protection methods and systems utilizing plant-based spatial repellents to fight the impact of malaria, West Nile virus, dengue fever and other mosquito-borne diseases. As another example, the present invention will make effective biological strategies available in the fight to control the spreading of serious invasive plant diseases, such as the citrus greening disease (Zaka et al., 2010) and the potato zebra chip disease (Miles, 2010).

It is to the provision of methods for delivering and maintaining volatile compounds meeting these and other needs that the present invention is primarily directed.

SUMMARY

Figure 1A:
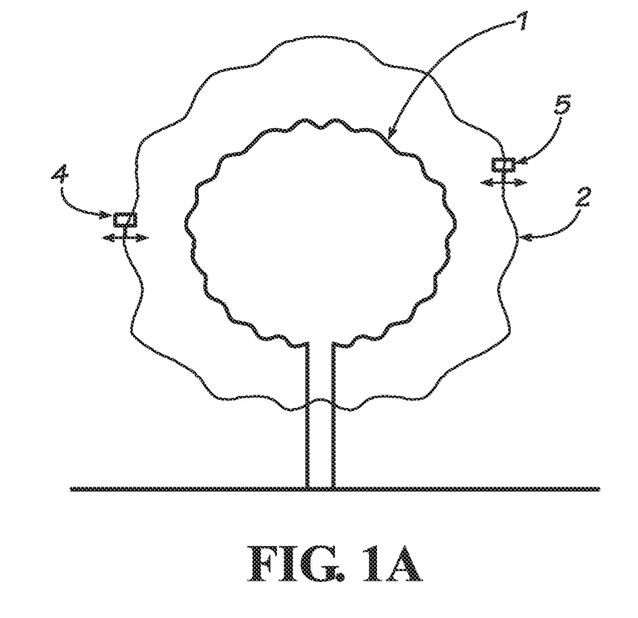
Figure 1B:
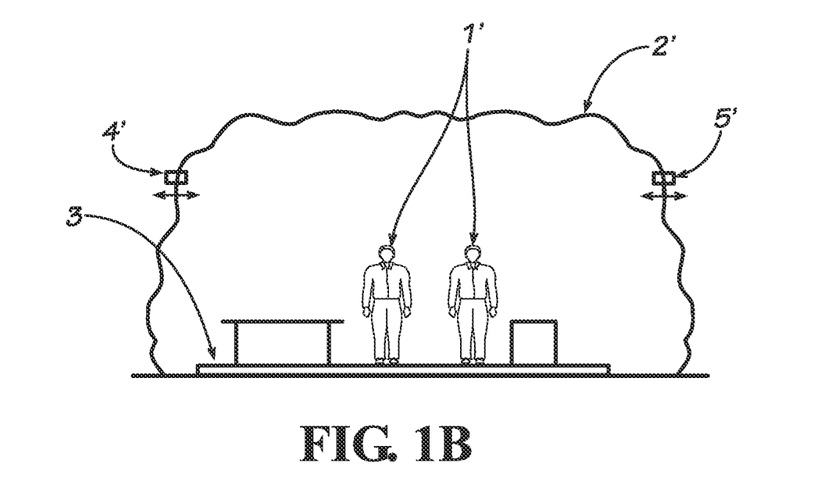

In example embodiments, the present invention comprises methods that, not only provide controlled delivery of one or more volatile compounds, but more significantly enable establishing and maintaining a geometrically shaped volume of volatile compounds whose concentrations are above the biologically effective threshold and encompass the object for which protection is sought in open outdoor environments over very long times. FIG. 1 shows examples of common geometrical shapes for typical applications among others that benefit greatly by providing an effective dynamic mixture, like a cloud, of volatile compounds such as repellents, etc. that surround an object and protect it from pests. Examples include young trees (spheroid shape) and patio or pavilion area (cuboid shape). Successful application of this novel protective concept requires three factors: balanced and controlled release rates, strategically positioned and uniquely oriented individual release sources and maintained pre-designed geometrically shaped volumes of volatile compounds in open outdoor environments.

In one aspect, the present invention comprises methods that provide balanced and controlled release rates of one or more volatile compounds at continuous, predetermined, substantially constant and sustainable levels to yield a product dispersion of ultra-low effective concentrations resulting in geometrically shaped volumes of volatile compounds over long time periods.

In another aspect, the present invention comprises methods that produce advantages in an open outdoor atmosphere having large volumes of moving air. The methods can provide controlled delivery at strategic locations that, in turn, yield effective concentrations in pre-designed geometrically shaped volumes of volatile compounds encompassing the object of protection in open field environments.

And yet another aspect, the present invention comprises methods which maintain the geometrically shaped volumes of volatile compound effective concentration for the required long time periods. To accomplish maintaining requires monitoring, replenishment and adjustment of release rates as required. Monitoring is accomplished by measurement of the insect response to the volatile compound or by measurement of the chemical concentration compared to the known effective level. Replenishment is accomplished by manually or continuously refilling the storage structures with volatile compounds. Based on the monitoring results the release rate of each individual passive flow control nozzle is adjusted to maintain the effective concentration for adequate protection of the object.

Briefly described in general terms, in a preferred form the invention comprises a method using a vapor delivery system including (a) plurality of passive flow control nozzles (nozzles) attached to a volatile compound-storing structure, wherein each nozzle is comprised of a mass-regulating polymeric barrier with retaining fixtures through which the volatile compound diffuses and is emitted from the outer surface into the atmosphere, and wherein the individual nozzles are designed to deliver a specific release rate, (b) combination of passive flow control nozzles in strategic positions and unique orientations to establish and maintain pre-designed geometrically shaped volumes of volatile compounds encompassing the object of protection, (c) compound-storing structures with replenishing connectors for volatile compounds, typically in liquid form, attached to the passive flow control nozzles, (d) appurtenances to protect the surfaces of the mass-regulating barriers while in operation as needed, (e) chemical sensors to monitor that the concentrations of specified volatile compounds are achieved within the boundary of the geometrically shaped volumes of volatile compounds encompassing the object of protection and (f) distinct sensors to monitor that the biologically effective threshold of volatile compounds is achieved within the boundary of the geometrically shaped volumes of volatile compounds encompassing the object of protection.

In another preferred form the invention comprises a method using a distributed system for applying a controlled amount of a volatile compound to an open outdoor area over a long period of time. The distributed system is configured as a network of passive flow control nozzles with the nozzles being linked by pipes to deliver the volatile compounds to the nozzles. The volatile compound can be replenished through the pipes of the distributed system by pumps, by gravity, or by other means. A common compound-storing structure is provided for delivering the volatile compounds from common compound-storing structure to the nozzles. A common compound-storing structure may supply one or more distributed systems. Optionally, different distributed systems may be combined to provide protection for the same or different objects.

The present invention also can take the form of a method using a system for applying a controlled amount of a volatile compound to an open outdoor area over a long period of time. The system includes a plurality of spaced-apart compound-dispensing nozzles, each compound-dispensing nozzle having a permeable membrane or material with retaining fixture permitting the volatile compound to pass therethrough by permeation at a substantially constant rate. A common compound-storing structure is provided for containing a supply of the volatile compound and a plurality of pipes extend to the nozzles for delivering the volatile compound from common compound-storing structure to the nozzles.

In one form, the present invention comprises a method for establishing and maintaining a pre-designed geometrically shaped volume of volatile compounds encompassing the object of protection for very long times. The method includes the steps of: (a) analyzing requirements of each specific application including, pest species, site environment, site topography and the object of protection, (b) designing an engineered vapor delivery system to accomplish desired protection for each specific application, (c) selecting required components and applicable volatile compounds to accomplish desired protection for each specific application, (d) fabricating passive flow control nozzles capable of delivering specified release rates of volatile compounds for each specific application, (e) assembling volatile compound-storing structures with replenishing connectors attached to the passive flow control nozzles, (f) positioning a plurality of passive flow control nozzles with specified release rates in predetermined strategic locations and unique orientations to create and maintain the pre-designed geometrically shaped volumes of volatile compounds encompassing the object of protection, (g) constructing on site the engineered vapor delivery system as designed, (h) filling the volatile compound-storing structures connected to the passive flow control nozzles, (i) installing mass-regulating barrier protection from external contamination when the system is in operation, (j) initiating start up of vapor delivery system operation, (k) monitoring that concentrations of volatile compounds are adequate within pre-designed geometrically shaped volumes encompassing object of protection, (l) monitoring that biologically effective thresholds are achieved within pre-designed geometrically shaped volumes of volatile compounds encompassing object of protection, (m) adjusting vapor delivery system components to obtain optimum performance throughout planned protection period, and (n) inspecting, refilling, cleaning, repairing and maintaining vapor delivery system as needed.

One application (among many) for the invention is a method to treat citrus trees or citrus groves. To that end, the invention also includes the method of treating citrus trees at risk of disease, infection, or infestation, etc. The method includes the step of placing a quantity of a selected volatile compound in a vapor delivery system having passive flow control nozzles connected and configured to allow the volatile compound to permeate there through at a low, substantially constant rate over long periods of time. The method also includes the step of placing nozzles on or near citrus trees to apply the volatile compound to the citrus trees and to their immediate surroundings for the duration of the desired treatment.

In another aspect, the invention relates to methods of preparing and using vapor delivery systems for biological control of pests and pest-borne diseases in a wide variety of practical applications including the protection of agricultural products such as fruits, vegetables, trees and flowers, the protection of people, pets, livestock, and the protection of grains/food stocks in transit and storage. The present invention is based on the concept of a practical means to utilize naturally derived volatile compounds from plants, including leaves, roots, wood, sap, bark, berries, seeds, etc., and then to employ those volatile compounds having known benefits in practical applications, such as biological pest control to protect humans, animals and plants through biological crop disease management in agriculture, forestry, horticulture and floriculture as well as landscape and ornamental plants. Among the benefits of biological control, especially when large-scale application systems, such as those of the present invention are implemented, will be reduced usage of various pesticides with significant reduction in pesticide residues in crop products, thereby also yielding overall environmental and food product safety benefits. Additionally using the invention to provide insect protection for humans, pets and animals will assist in the battle to decrease sickness and death caused by insect-vectored diseases.

Preferably, the methods of the present invention provide a continuous, predetermined, substantially constant and sustainable rate of delivery over extended periods of time, and achieve ultra-low effective concentrations in the ambient atmosphere of open environments subject to moving air currents. The approach employed in the present invention employs passive flow control nozzles with mass-regulating barriers or materials with retaining fixtures.

The present invention represents a break-through in the art of controlled delivery of volatile compounds in several aspects. Indeed, the vapor delivery methods of the present invention described herein can: (a) provide controlled rates of delivery at predetermined strategic locations which establish and maintain desired geometrically shaped volumes of an effective dynamic mixture of volatile compounds encompassing the object of protection, (b) provide, over entire seasons that can last many months up to and exceeding one year, rates of delivery that are continuous, predetermined, substantially constant and sustainable, (c) provide protection from pests and pest-borne diseases within open outdoor environments over much larger areas than can be accomplished by prior art, (d) provide fine-tuning or adjustment of the rate of delivery for specific applications in response to effectiveness monitoring, (e) provide flexibility to utilize diverse groups of volatile compounds having vapor pressures that range over several orders of magnitude and (f) permit deployment of enhanced biological-control strategies.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 1A and 1B are schematic illustrations of two typical shapes: a spheroid of volatile compounds encompassing the object tree and a cuboid of volatile compounds encompassing the object patio.

FIG. 2A is an exploded cross-sectional view of an example form of a vapor delivery system component of the present invention where liquid is in contact with the mass-regulating barrier.

FIG. 2B is an exploded cross-sectional view of another example form of a vapor delivery system component of the present invention where vapor is in contact with the mass-regulating barrier.

FIG. 3 is a schematic view of an example vapor delivery system of the present invention, deployed in a notional (agricultural) grove plot plan.

FIG. 4A is a schematic illustration of another example vapor delivery system component of the present invention.

FIG. 4B is a schematic illustration of another example vapor delivery system component of the present invention.

FIG. 4C is a schematic illustration of another example vapor delivery system component of the present invention.

FIG. 4D is a schematic illustration of another example vapor delivery system component of the present invention.

FIG. 5 is a graph schematically depicting a comparison of the delivery rate of a volatile natural compound versus time for one tested embodiment of the present invention in comparison to the performance of a prior art technology.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific methods, systems, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "open environments" as used herein refers to environments subject to large-scale moving air currents as opposed to restricted spaces such as a room, closet, etc. Distinction, however, must be made between open local environments and open field environments. The former refers to relatively small air volumes including but not limited to single trees, individual landscape or garden plantings, and near outside doors, windows or entryways. Additional example open local environments include pavilions, decks, patios, docks, home gardens, nurseries, and greenhouses. Enclosures for storage of foodstuff or feeds within silos can also be considered as open local environments because they are not perfectly sealed, but leak air. These situations are in marked contrast to open field environments that include large agricultural and floricultural fields, citrus groves, orchards, vineyards, etc.

The term "volatile compounds" as used herein refers to organic compounds or materials that are vaporizable at ambient temperature and atmospheric pressure without the addition of energy by some external source. Any suitable volatile compound in any form may be used. Volatile liquids composed of a single volatile compound are preferred for large-scale application, but volatile solids can also be used for some specialized applications. Liquids and solids suitable for use may have more than one volatile component, and may contain non-volatile components. The volatile compounds may be commercially pure or blended and, furthermore, may be obtained from natural or synthetic sources.

In the context of the methods described, the term "vapor delivery systems" as used herein refers to those vapor delivery systems that are based on passive flow control nozzles that utilize mass-regulating barriers. There are two primary preferred approaches in the present invention—manually replenished systems and distributed replenished systems (such as replenished by gravity or by pumps). Vapor delivery systems that are manually replenished are used to deliver volatile compounds in either open local environments or open field environments. On the other hand, distributed replenished systems with a piped distribution header are uniquely suited for applications in open field environments. These preferred approaches are classified as passive systems since the vapor that results from volatilization at the barrier surface is dispensed by stagnant diffusion and/or random air circulation over the nozzles. The pump or gravity is only used to deliver the volatile compounds from a common compound-storing structure to the nozzles.

The term "geometrically shaped volumes of volatile compounds" as used herein refers to a special connotation different than the typical view of the dispensing of spatial repellents into three-dimensional spaces. First and most specifically, there is a key aspect of control and maintenance that has been unachievable in the prior art, namely, dispensing and controlling the distribution of volatile compounds in the atmosphere forming distinct geometrical shapes that generally align with the object to be protected over very long times. Long-term protection of objects in open outdoor environments requires (a) continuous and controlled release of an effective spatial repellent and (b) continuous and controlled encompassing or surrounding the object of protection by the dispensed volatile compounds for up to one year or longer. From a visualization perspective, it is as if the object is in a "protective cloud" of invisible volatile compounds that effectively repel any targeted pests attempting to enter the zone of protection. The peripheral boundary is not abrupt; instead it is dynamic, shifting back and forth about a mean surface by convective air currents. The boundary, albeit diffuse, occurs where the concentration of volatile compounds falls below that of the biologically active threshold, and beyond which the volatile compounds become ineffective. The establishing and maintaining of a "protective cloud" of arbitrary, but designed shape (e.g., spheroid, cuboid) encompassing the object of protection is achieved by strategic positioning and unique orienting of individual passive flow control nozzles, whereas each nozzle dispenses its volatile compounds at the designed predetermined release rate, and whereas the combined effect of the passive flow control nozzles taken together yields the effective zone of protection, with approximate shape, spatial area and volume desired, for targeted pests with specific volatile repellent compounds.

The term "effective dynamic mixture" as used herein refers also to the visually descriptive phrase "protective cloud" but with more emphasis on effective concentration. In other words, the concentration of volatile compounds is above that of the biologically active threshold for insect response that then defines the dynamic boundary of the "geometrically shaped volume of volatile compounds".

The term "passive flow control nozzles" as used herein refers to a mass regulating material or barrier with a retaining structure that together constitute the nozzle that controls the rate of delivery of volatile compounds by means of a diffusive mass transfer process. The mass-regulating barrier can take various geometrical forms (flat or cylindrical) depending on the configuration. The flat barrier is used with a retaining band or fitting that allows control of the exposed surface area. The distributed replenished systems can be designed such that the piping itself or sections of the piping, if constructed of select permeable polymeric material, are able to function as passive flow control nozzles separate from or in addition to flat mass-regulating barriers.

For a more complete understanding of the present invention and its potentialities, it is useful to briefly examine diffusion processes in nonporous and porous solids in the context of the manually replenished vapor delivery systems. In vapor permeation, the vapor of a volatile compound is in contact with a homogeneous permeable solid. The molecules in the vapor phase first dissolve in the solid, then diffuse through the solid by a Fickian diffusion process, next vaporize at the solid surface and finally diffuse and mix in the open environment via convective mass transfer processes. In the case of a vapor in equilibrium with its liquid phase, the vapor pressure of the volatile compound—and thus the release rate—will be constant for a given temperature. In liquid permeation, the liquid phase instead of the vapor is in contact with the homogeneous permeable solid. The molecules of the liquid phase dissolve at higher concentration before diffusing through the solid to the open environment. On the other hand, in the case of porous solids, Knudsen diffusion can take place in the pores, or a combined Fickian-Knudsen diffusion process can occur depending on the solubility of the volatile compound in the mass-regulating barrier material.

Prior to a detailed description of the invention, it is beneficial to examine the design considerations underlying the development of a vapor delivery system to achieve the requirements set forth earlier in the 'Summary'. Factors that must be considered to design a vapor delivery system for a given volatile compound include the chemical composition of the mass-regulating barrier and its physical structure, its surface area, thickness, contacting phase, temperature, pressure and dimensional stability. Mass-regulating barriers can be constructed of single or multiple layers. Knowledge of the prevailing airflow and ambient conditions at the site of deployment of a volatile compound delivery system is also essential for optimal system design.

To validate the performance of a polymeric vapor delivery system using a selected volatile compound, laboratory tests under controlled conditions were performed to evaluate whether the concept is both applicable to the needs and that a sustained, substantially constant release rate can be maintained for long periods of time. Mass-regulating barriers made from off-the-shelf materials were tested to evaluate the release rates for a range of surface areas and barrier thicknesses. Evaluations using both liquid and vapor phases in contact with the barrier materials were performed.

The performance of a mass-regulating barrier is strongly dependent on its chemical and physical properties and its structure. The chemical interactions between the barrier material and the volatile compound determine the solubility and permeability of the molecules diffusing in the solid matrix. In the case of polymeric mass-regulating barriers, the molecular weight, crystallinity, density and dimensional stability are also important considerations in material selection. Furthermore, the phase of the volatile compound in contact with the mass-regulating barrier, either vapor or liquid, is an important design parameter because the concentration adjacent to the barrier surface establishes the driving force for diffusion. The barrier thickness is another important design parameter since the release rate is also determined by the resistance to diffusion in the solid, and the resistance can be controlled by selection of material, selection of thickness and/or design of stacked or spaced apart barriers.

In one application, the mass-regulating barriers employed in the present invention are preferably nonporous, homogeneous solids and are selected to yield the desired release rate for the specific volatile compounds. The composition is typically that of a solid polymeric material, either natural or synthetic. Some selected examples include but are not limited to polypropylene, polyethylene, copolymers of ethylene or propylene, cellulose acetate, polyacrylonitrile and copolymers of acrylonitrile, ABS, polyesters including polyethylene terephthalate, acetal copolymers, polycarbonate, poly(4-methylpentene-1) and various fluorocarbons. For other applications, the use of a porous material may be advantageous for fine-tuning a release rate. Such a mass-regulating barrier is designed to be vapor permeable and liquid impermeable. As an example, a microporous material with select hydrophobic and oleophobic properties may be substituted for a nonporous barrier to provide an increase in release rate or to modify a release rate for a given volatile compound to achieve a designed release rate.

It is well known that temperature affects the release rate of volatile compounds, and the present invention exploits this effect in a novel manner in some applications. The effect of temperature on the release rate can arise from two sources, one is related to the temperature dependence of the intrinsic permeability of barrier materials, and the other is the effect of temperature on vapor pressure. In one specific application, the release rate is designed for an average rate over a growing season or part of a growing season when pests or insects are most active. In this situation, the passive flow control nozzles are "self regulating" in that the release rate automatically increases with higher temperatures coinciding with increased pest activity; therefore more volatile compound is made available for control. On the other hand, less volatile compound is naturally released during lower temperatures when pests are less active. For some insects that impact animals and humans, this benefit can also be realized. In applications where temperature variation has an undesirable impact on the release rate, other parameters can be adjusted to compensate. Pressure is one such parameter that can be monitored and adjusted in real time to fine control the release rate for many applications.

The particular details of the open environment surrounding the vapor delivery system play an important role in the overall performance and cost-effectiveness of the system and therefore influence its physical configuration. The scale of the system is defined by its parameters such as spatial extent, individual and total release rate, and nozzle density, and correlates with the scale of the environment over a range from local to field. Permanency and maintainability of the installed vapor delivery system are also a consideration, and depend on the temporal scale of the intended application. Many volatile compounds are highly diffusive in air, and the motion of the air is driven by forced and natural convection processes and influenced by boundaries and structures. For a specific release rate and points of release, the combination of convective properties of the flow and diffusive properties of the vapor is the determining factor in the concentration of the volatile compound within the open environment. Therefore, the system should allow for release points that can be configured and reconfigured depending on airflow conditions or optimized over a range of airflow conditions. The system should also allow for the release of different volatile compounds in different regions of the open environment when a specific application warrants such a complementary combination.

Monitoring the dynamic boundary of the geometrically shaped volumes of volatile compounds is one of the keys to success in attaining the desired effective impact on the targeted pests. At least two types of dynamic boundary monitoring are available. The first is accomplished by monitoring, using such as differential ion mobility spectrometry, the concentration level of the selected volatile compound in the immediate surroundings of the object by moving the instrument-sampling intake from inside the volume outward until the reduced concentration is observed at the level previously determined to be effective for that particular volatile compound on the specific targeted pests. Repeating this procedure in different directions from the object of protection establishes the effective dynamic boundary for the existing conditions. The second type monitors the biologically active threshold of targeted insect response to the volatile compound, using such as electroantennography. Repeating this procedure in different directions as in the first type establishes the effective dynamic boundary. Thereupon, responding to the information determined from one or both monitoring types, adjustments are made to the passive flow control nozzles to optimize and maintain the desired effective dynamic boundary relative to the object of protection.

FIGS. 1A and 1B depict schematic illustrations of typical objects to be protected. The first object is a tree 1 with a spheroid of protective volatile compounds 2 encompassing the tree (FIG. 1A). Measuring devices 4 for concentrations of the selected volatile compound and 5 for biological active threshold are used to optimize and maintain the desired effective dynamic boundary relative to the object of protection. The second object is a deck or patio 3 with people 1' and a cuboid of protective volatile compounds 2' encompassing the deck 3 and the people 1' (FIG. 1B). Measuring devices 4' for concentrations of the selected volatile compound and 5' for biological active threshold are used to optimize and maintain the desired effective dynamic boundary relative to the object of protection. In each example the shape of the effective dynamic mixture of volatile compounds required to protect the object is established and maintained for the duration of the desired protection. This is a visual representation of what is happening around the object that is protected. Actually the volatile compound is invisible, but its presence can be monitored. The volatile compound is effective out to the dynamic boundary where the level of volatile compound drops below that which is required to cause the pests to perform the desired responsive action.

Figure 2A:
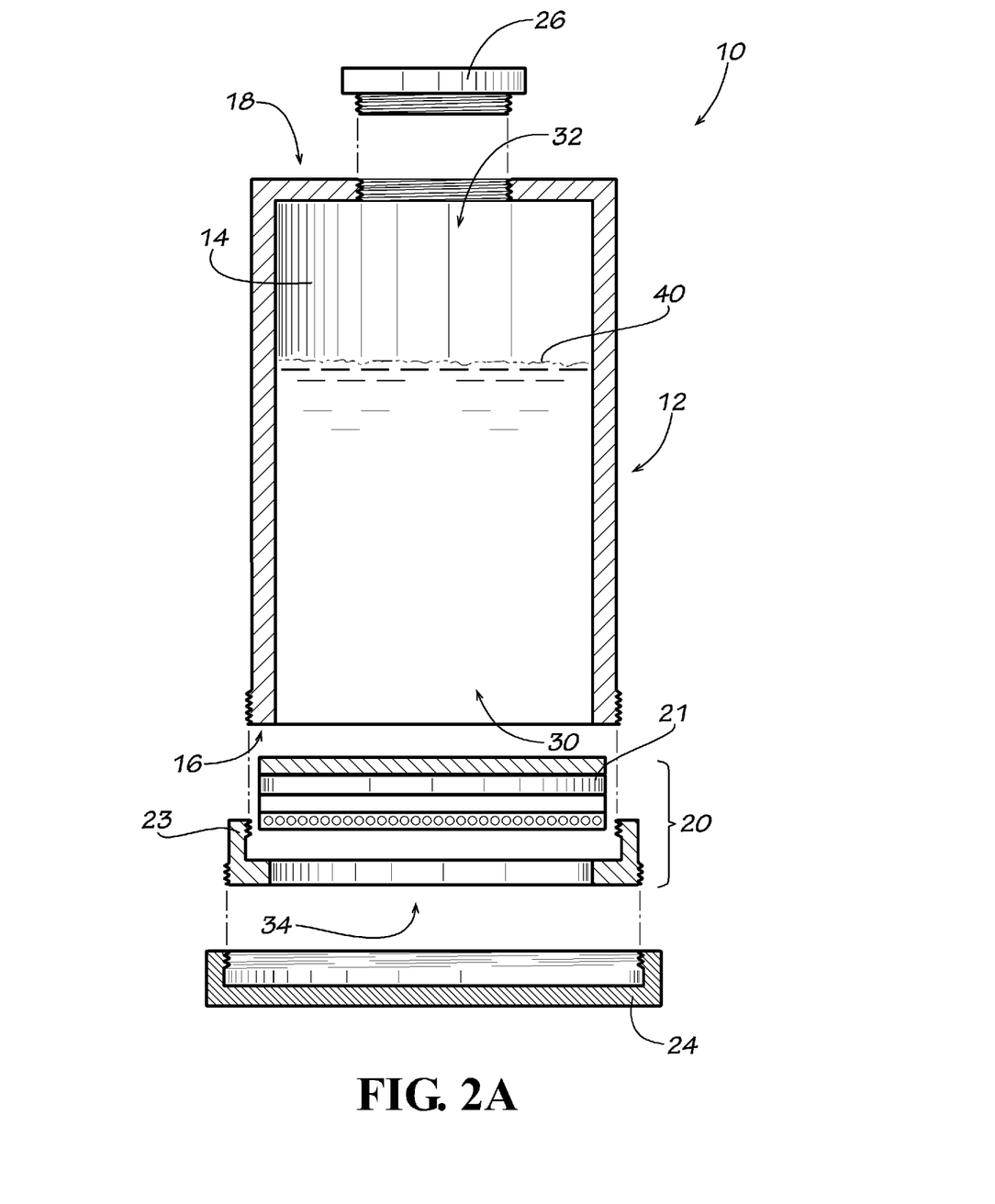

FIG. 2A depicts a component 10 of a manually replenished vapor delivery system. In general, the component 10 comprises a compound-storing structure 12 and passive flow control nozzle 20. The compound-storing structure 12 defines an internal elongated cavity 14 that stretches from a first end 16 comprising an opening 30 to a second end 18 (see FIG. 2A). The passive flow control nozzle 20, in its simplest form, comprises a flat mass-regulating barrier 21 and a retaining band fastener 23. The flat mass-regulating barrier as depicted reflects a second layered mass-regulating barrier in contact and a third mass-regulating barrier spaced apart from the two mass-regulating barriers in contact. The retaining band fastener 23 has an open area or aperture 34 of predetermined dimensions through which the vapor emitted from the barrier surface passes prior to mixing with the ambient atmosphere. The mass-regulating barrier 21 is positioned between the compound-storing structure 12 and the retaining band 23 to attach the barrier to the compound-storing structure when the band is removably coupled to the first end 16 of the compound-storing structure. Alternatively, the second end 18 of the compound-storing structure 12 can comprise a supply port 32 used for filling (and refilling) the compound-storing structure with the volatile liquid upon the removal of a filler plug 26 (see FIGS. 2A-B). FIG. 2A illustrates the form of the component with liquid in contact with the mass-regulating barrier. For any particular volatile compound, the rate of release and the resulting local vapor concentration depend on the choice of the barrier material used, its thickness, and area of exposed surface. The lifetime of a specific vapor emission is determined by the quantity of volatile liquid in the compound-storing structure, and thus a sustained rate of release for an extended period of time can be achieved by increasing the capacity of the compound-storing structure. Unless additional permeation is needed, the compound-storing structure is made of a material impervious and typically non-reactive to the contents of the compound-storing structure. In some applications it may be desirable to employ materials that are biodegradable.

Figure 2B:
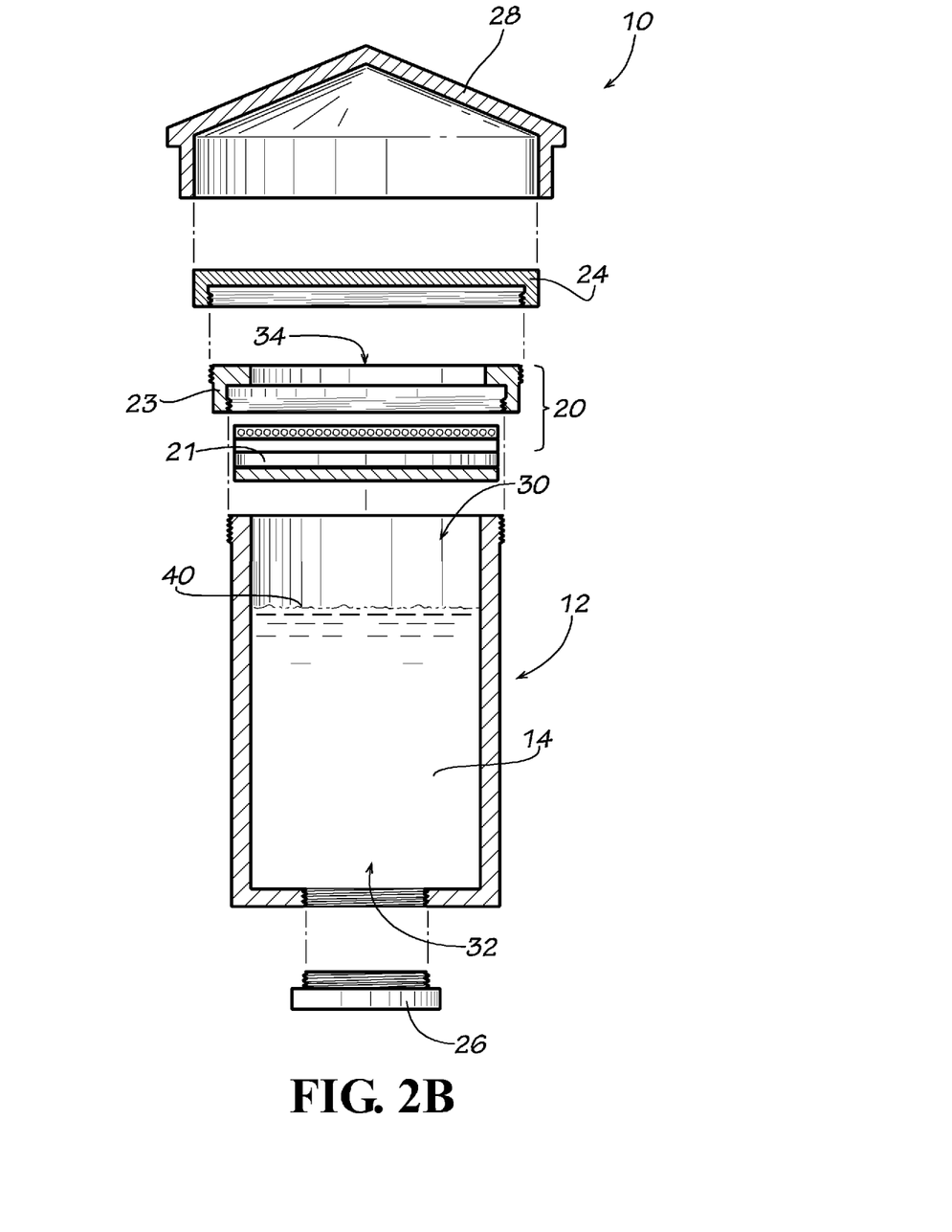

FIG. 2B illustrates another form of the component 10 with vapor in contact with the mass-regulating barrier 21. The flat mass-regulating barrier as depicted reflects a second layered mass-regulating barrier in contact and a third mass-regulating barrier spaced apart from the two mass-regulating barriers in contact. For example, the compound-storing structure depicted in FIG. 2B contains a vaporizable liquid in equilibrium with its vapor as shown schematically by the existence of a vapor-liquid interface 40. Additionally, a sealing cap 24 can be removably coupled to the retaining band 23 when shipping the component with volatile compound or when not in active use. When the components 10 of the vapor delivery system are in active use, a debris cover 28 may be mounted to the retaining band 23 if site conditions warrant. The resulting release rate when liquid is in contact with the barrier is greater than that when the vapor phase is in contact with the barrier. Furthermore, it may not be necessary to use a debris cover to protect the passive flow control nozzle from harmful contamination. It may be advantageous in some applications to maximize vapor release area by replacing a portion or all of the compound-storing structure with a cylindrical mass-regulating barrier (not shown).

The uniqueness of the manually replenished approach is its flexibility, portability, and versatility. This approach may utilize a modular self-contained package that is easily installed and requires no power source to function effectively. It is capable of serving multiple applications such as single plants, forests, landscaping, gardens, nurseries, open fields, citrus groves, residential citrus trees, grains and foodstuff in storage or transit as well as human and animal pest control. Its performance in dispersing volatile compounds makes enhanced biological control available to a wide range of type and size of applications.

Figure 3:
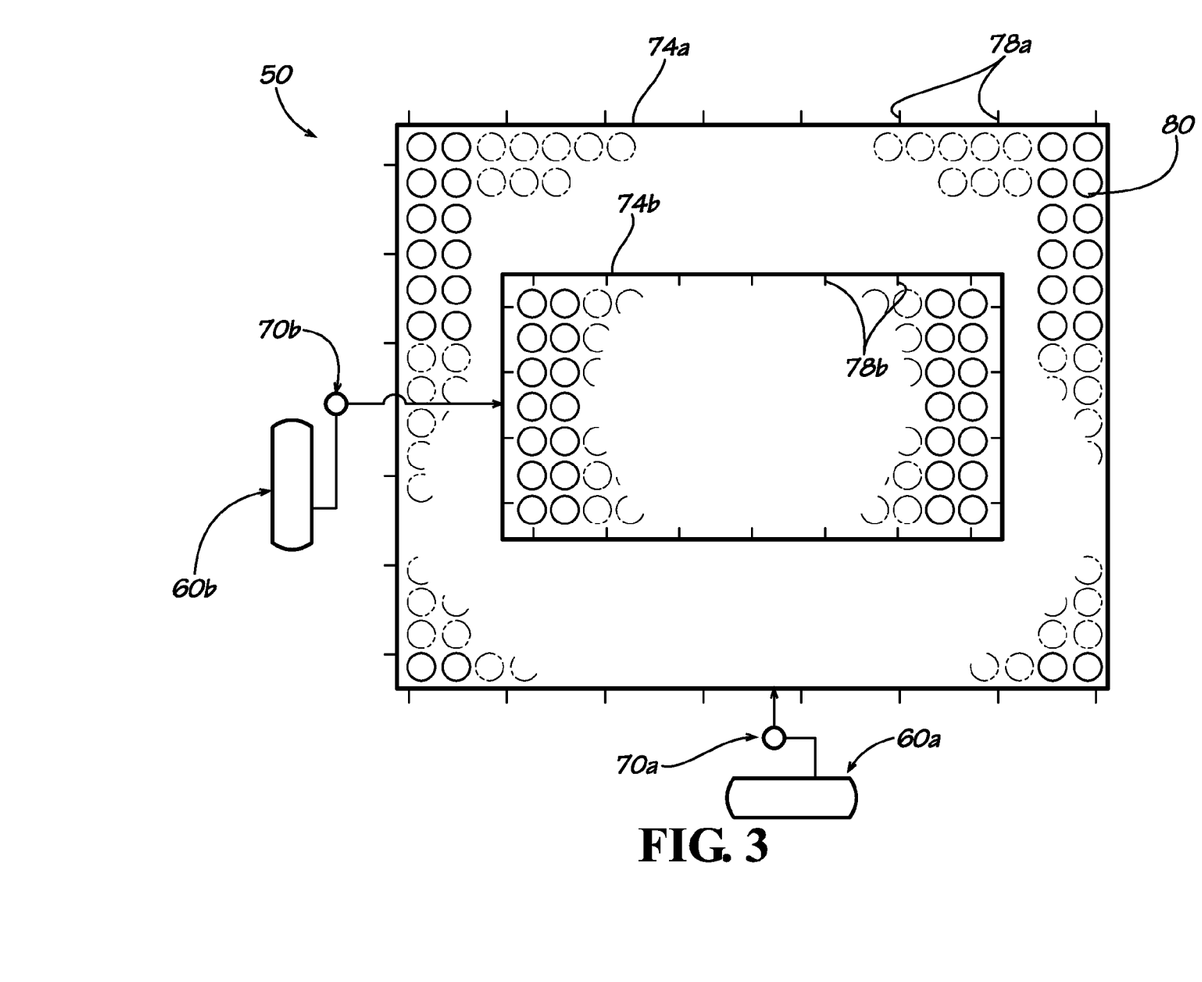

In another preferred embodiment, methods using a pumped (distributed) vapor delivery system are employed in an open field environment. FIG. 3 illustrates a pumped system 50 comprising a common compound-storing structure 60a and a pump 70a. The common compound-storing structure 60a contains and supplies the volatile compound that is to be released from the passive flow control nozzles into the atmosphere. The pump 70a, in fluid communication with the common compound-storing structure 60a, is further engaged to one or more distribution headers 74a comprising a plurality of nozzles 78a. The pumped system 50 is uniquely suited for applications in open field environments, especially large acreages of plants or crops that require the controlled release of a volatile compound from multiple sources strategically placed and uniquely oriented in order to provide a predetermined effective concentration in the ambient atmosphere. This illustrated pumped system could also be a gravity system, referred to elsewhere herein as a distributed system. This approach to the delivery of volatile compounds makes possible the practical application of enhanced biological control strategies in agricultural fields, groves or orchards.

In yet another preferred embodiment, methods using multiple pumped systems are employed in an open field environment. FIG. 3 schematically illustrates the deployment of two pumped systems for the implementation of a specific biological control strategy. The multi-system configuration additionally shown in FIG. 3 permits the release of volatile compounds for an enhanced biological control strategy hereafter called a "repellent-attractant strategy" or a "push-pull strategy". In the model grove plan shown in FIG. 3, the piping of the first pumped system for the distribution header 74a is situated at the perimeter or border to release a repellent compound for the purpose of repelling or keeping pests from entering the grove and, hence, protecting the grove plantings 80 from attack by specific pests or pests in general. The second pumped system comprising a common compound-storing structure 60b, a pump 70b, a distribution header 74b, and a plurality of nozzles 78b is located within the interior of the grove. The second pumped system can dispense an attractant compound that attracts beneficial insects or organisms and/or assists in the promotion of inducing resistance that helps plants resist and recover from diseases. Thus, by using different volatile compounds in each respective system, it provides the capability to achieve enhanced biological control through the synergistic reaction of the two individual volatile compounds. This also is applicable to gravity systems.

Figure 4A:
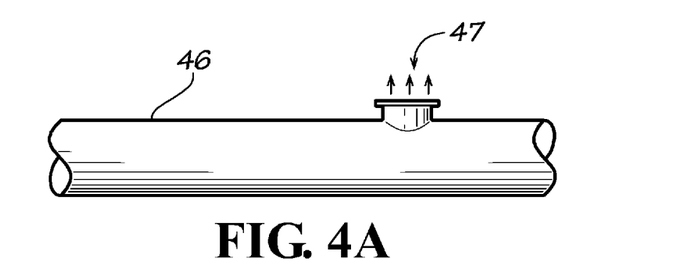
Figure 4B:
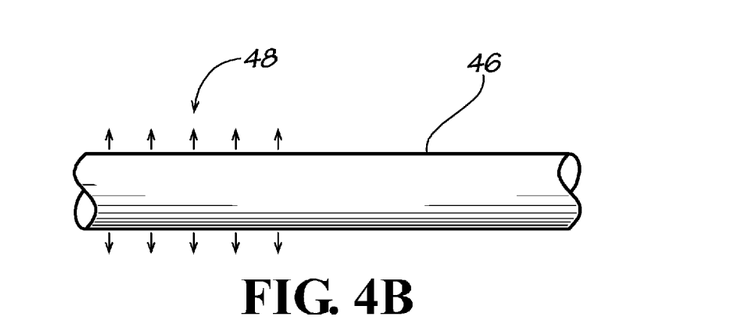
Figure 4C:
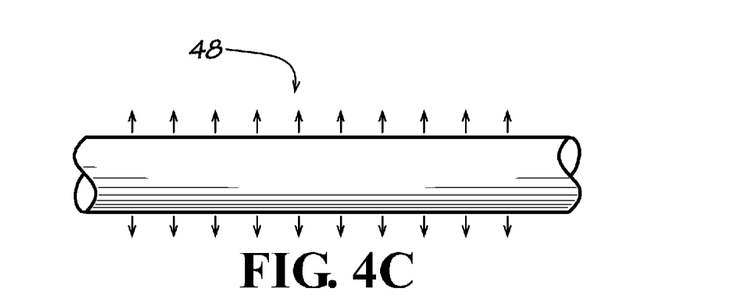
Figure 4D:
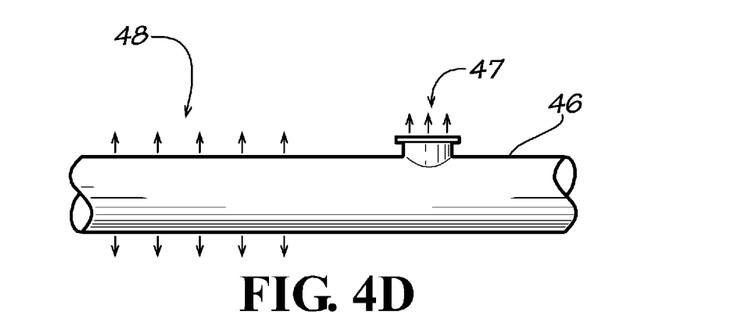

There are at least four configurations of passive flow control nozzles that can be utilized to release volatile compounds in pumped systems. FIG. 4A illustrates a section of the pumped system consisting of impermeable piping 46 and flat mass-regulating barriers 47. FIG. 4B illustrates a section of the pumped system consisting of alternating lengths of impermeable piping 46 and cylindrical mass-regulating barriers 48. FIG. 4C illustrates a pumped system wherein the entire piping of the supply header consists of a cylindrical mass-regulating barrier 48. FIG. 4D illustrates a combination of the above configurations.

For a specific volatile compound, the flexibility associated with the design of a vapor delivery system for a particular application permits virtually any desired individual and system release rates to be achieved in practice. This is accomplished by diligent analysis of the specific application requirements and then proper selection of the mass-regulating barrier material(s), thickness and the barrier surface area via a combination of flat and cylindrical mass-regulating barriers that are strategically located within an open field environment, considering the local ambient conditions, to yield an effective concentration of volatile compounds. The design of a vapor delivery system is not limited to only one barrier material. Fine tuning of the system release rate can also be achieved by the use of more than one barrier material and barrier type.

In another preferred embodiment, methods using any number of distributed systems are employed to release any number of volatile compounds for any combination of repellents, attractants, interference agents, immune enhancement promoters, or other volatile chemicals for any purpose that may or may not be related to the implementation of enhanced biological control strategies.

In still another preferred embodiment, methods using manually replenished systems can also be employed in open field environments either alone or in combination with distributed systems. The piping of the distribution header in distributed systems can also function as a mass-regulating barrier, if its chemical and physical properties are properly considered, for the volatile compound used. The passive flow control nozzle, as defined earlier, consists of a flat permeable mass-regulating barrier connected to a retaining structure, such as a retaining band or a fitting. In the case of a permeable pipe, structure is built into the cylindrical pipe wall (or barrier), and as such, the piping itself can be considered to be a passive flow control nozzle. The relevant surface area to be used in calculations of the actual release rate of the volatile compound is the surface area of the length of piping employed as the passive flow control nozzle.

The present invention has many advantages, one of which is the flexibility the methods offer in the design and engineering of vapor delivery systems that release volatile compounds in such a manner as to maintain pre-designed geometrically shaped volumes of an effective dynamic mixture of volatile compounds encompassing the object of protection in open environments for very long times. This flexibility originates in the plurality of passive flow control nozzles employed. In addition, the strategic positioning or placement and unique orientation of passive flow control nozzles are additional components of the flexibility advantage. The passive flow control nozzle approach permits design of a vapor delivery system that emits a predetermined release rate from the individual nozzles for a specific application of a volatile compound. The combination of individual release rates permits the obtainment of the effective concentration above the biologically active threshold in the pre-designed geometrically shaped volumes of volatile compounds that encompass the object of protection. It should be emphasized that the release rates from a nozzle and a system are different. The total release rate of a vapor delivery system is the sum of the individual release rates from the nozzles making up the system as a whole.

EXAMPLE APPLICATIONS

Examples are provided that demonstrate the methods and systems of the present invention are successful in practice. Firstly, it is shown that the release rates of volatile compounds using passive flow control nozzles can be made substantially constant over very long times. Secondly, the mosquito tests show that excellent protection from biting insects such as mosquitoes can be achieved in large open environments over very long times using the methods and systems of the present invention to establish and maintain pre-designed geometrically shaped volumes of effective dynamic mixtures of volatile compounds encompassing virtually any practical object of protection. Thirdly, the methods and systems are applied to a practical agricultural problem and the art of how to provide protection for citrus plants from the vector of HLB or citrus greening disease. Fourthly, the methods and systems are shown to be advantageous as a successful alternative approach to insect baiting and trapping. Fifthly, and lastly, several food industry applications of the methods and systems are presented herein.

Example 1

Figure 5:
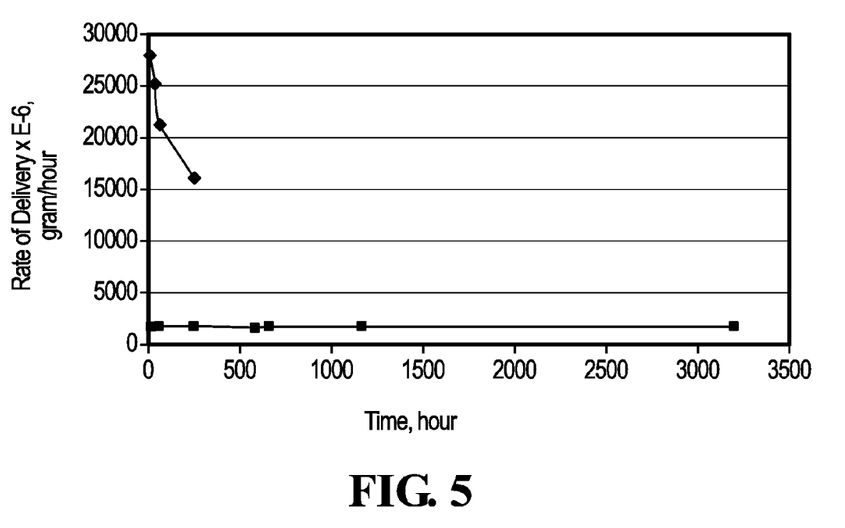

Representative laboratory test results are presented in FIG. 5 and confirm that a substantially constant release rate over a long period of time, displayed by the lower curve, is attained. The upper curve depicts an example of the unsuccessful existing state of the art open evaporative process, which reflects the high rate of release and the short duration of time. Comparison of the two curves demonstrates that the desired requirements for vapor delivery by the use of passive flow control nozzles can be achieved.

Experimental release rates of a volatile compound from a model manually replenished system were measured as a function of time. Glass screw-thread sample vials with PTFE/silicone septa and open-top polypropylene caps contained the volatile liquid compound. Two different sizes of vials were employed: small 8 mL capacity (17 mm O.D. and 63 mm height) and large 40 mL capacity (28 mm O.D. and 98 mm height). The test volatile compound selected for study was dimethyldisulfide (DMDS). Duplicate samples of 5.5 mL and 30 mL of DMDS were added to the small and large vials, respectively. Then a mass-regulating barrier was placed on the top of each vial, and the open-top cap was tightly screwed to seal the vial contents. The diameters of the mass-regulating barriers for the small and large vials were 13.4 and 22.0 mm, respectively. In addition, the diameters of the openings in the caps for the small and large vials were 8.78 mm and 14.62 mm, respectively. Each vial with barrier, cap and liquid contents was then immediately weighed on an analytical balance. Next, the vials were placed in a dedicated laboratory fume hood. Ambient air with a bulk velocity of about 1.4 m/s (or 3 mph) passed over the vials. The targeted air velocity is representative of the average air velocity at the closest weather station to a planned grove test site over a one-year period. At selected times the vials with barrier, cap and liquid were weighed to obtain the mass loss of the vial contents as the volatile compound permeated through the mass-regulating barrier of the vial over time. From these primary measurements the release rate for each nozzle was determined as a function of time.

Permeation rates were obtained for a variety of barrier materials including low-density polyethylene (0.004), acrylonitrile butadiene styrene (0.003), polyethylene terephthalate (0.003), polymethylpentene (0.003), polytetrafluoroethylene (0.003), polycarbonate (0.040), acetate (0.010) and acetal copolymer (0.010). The numbers in parentheses represent the thickness stated in inches. In addition, the effect of barrier thickness was examined by using low-density polyethylene (0.004 and 0.010), high-density polyethylene (0.015 and 0.030), and ultrahigh-molecular weight polyethylene (0.005, 0.010 and 0.020).

FIG. 5 shows the release rate performance of a representative barrier material (low-density polyethylene, 0.004 inch-thick). The laboratory measurements confirm that a substantially constant release rate (26 mg/day) is attainable over an extremely long period of time. While this test lasted for 133 days in the laboratory, field tests have demonstrated that this rate may continue for over one year. Thus, dramatically improved results over the known prior art can be achieved when using the vapor delivery method and system of the present invention.

Example 2

Insects such as mosquitoes, fleas, biting flies and ticks transmit many human diseases that can be debilitating and deadly. World-wide, and particularly in Africa, many children are dying each day from malaria. Using the methods and systems of the present invention with the correct volatile compound(s) opens up the opportunity to assist in the battle against many vector-borne diseases. The success of recent mosquito field tests demonstrates that this application of the present invention has the potential of reducing much sickness, suffering and death.

Mosquito control tests were conducted with plant-based spatial repellents in Florida and Ohio in 2012 and 2013 at locations infested with high populations of mosquitoes such that, upon going outside without mosquito bite protection, mosquito bites would occur within about one minute. The site locations and protected areas were as follows: Lakeland, Fla., 40 ft×25 ft, social pavilion; Orlando, Fla., 60 ft×35 ft, large deck with pool; Oakland, Fla., 27 ft×18 ft, deck and outside door entryway; Stow, Ohio, 12 ft×18 ft, deck. There are numerous weekly gatherings of people both inside the social pavilion and just outside its periphery. The mosquito control effected by the mosquito repellency method and system has been exceptional, typically no mosquito bites whatsoever, and only twice in over 5 months in 2012, one or two bites at an event dependent on particular host odors or fragrances used by guest. Tests at the other sites were also highly successful, even though mosquitoes were abundant in the surroundings beyond the protected area. Importantly, the protection until the end of 2013 at three Florida sites has been effective for seven (7) months and is still in progress at all sites. Significantly, the extent of protection coverage is excellent, up to 2500 sq. ft. The mosquito repellency method and system provided the desired level of mosquito control at this stage of development, even though not yet optimized.

Further field tests were performed to evaluate the vapor delivery method to repel mosquitoes at a home in Oakland, Fla. by installing a manually replenished system under the eve over the front door. This home is located in a wooded lot and has hedging along both sides of the front walk extending from the front door out to the drive. The residents have a German Shepard dog that requires walking several times a day and sometimes during the night. Each time the dog was walked, the mosquitoes would attack both human and animal. The results were both bites and bringing mosquitoes in the house on their clothes and on the dog. After installing the system under the house eve, the mosquitoes decreased to where they were no longer a problem around the front door. In marked contrast, mosquitoes were observed in the yard during this time. This positive result continued for more than one year. Mosquito presence was verified in the nearby front yard by placing pans of water where larvae were observed in a few days. The vapor delivery method and system of the present invention is effective in repelling these mosquito species in a residential application with the appropriate volatile compound.

Example 3

One ready application of the present invention is to repel Asian citrus psyllids and provide annual protection for citrus "resets", new plantings, young trees (4-7 years) and citrus groves against Huanglongbing (HLB) disease (and other citrus diseases as appropriate). A citrus reset is a replacement for a single existing tree. Typically, it is about 18" high. As presently considered, a manually replenished system with a plurality of passive flow control nozzles shall be installed per reset at planting. The citrus resets usually do not produce fruit in the first three years. However, in years 2 and 3, it may be desirable to install additional passive flow control nozzles.

In the context of citrus, a "new planting" is when one plants an entire new grove (or large area), typically with the above 18" high resets. Once again, the plantings usually are not productive for the first three years of growth. A "young tree" or young trees are productive trees of 4-7 years of age. They are fruit bearing and continue to grow in height and width. Thus, an increase in the manually replenished systems or a distributed system will often be required. The number, strategic location and unique orientation of passive flow control nozzles required will be based on an engineering design for a particular site and grove. A "grove" typically consists of a large array of productive mature trees whose age is eight or more years. The present invention can provide perimeter control, grove control or combination control of repellents, attractants and various promoters or interference agents (e.g., mating and reproduction interference, plant immune enhancement, etc.).

The present invention can deliver volatile repellent compounds in either open local (single tree) or open field (grove) environments and help address the HLB crisis. One application concentrates on protecting citrus resets that are in the life stage of a tree that is most vulnerable to disease. If the growers cannot successfully grow resets to productive maturity, the industry is headed to extinction because of the need to plant new groves and to replace trees removed from existing groves due to canker, blight, black spot, HLB and other impacts. One potential impact of the present invention is to allow citrus resets to be grown to productive maturity without frequent use of pesticides. This allows the growers to again prudently invest in resets to give new life to the industry, stabilize and then grow the production of citrus with the resulting economic benefits to the growers and to the customers of citrus products that have reduced pesticide residue.

It is expected that psyllid control can be achieved with greatly reduced use of pesticides for citrus resets (and new plantings) by employing the manually replenished methods and systems that release volatile repellent compounds which are behaviorally efficacious under field conditions over entire (annual) growing seasons. It is also expected that psyllid control can be achieved with greatly reduced use of pesticides for young citrus trees by employing the manually replenished methods and systems that release volatile repellent compounds which are behaviorally efficacious under field conditions over entire (annual) growing seasons. It is also expected that psyllid control can be achieved with greatly reduced use of pesticides for developing productive citrus groves with a perimeter (vapor) barrier to repel the influx of psyllids into groves. This outcome will favorably impact the citrus growers and provide them an alternative or supplement to the numerous repeated pesticide spraying now used. Finally, it is expected that psyllid control can be achieved with greatly reduced use of pesticides within the interior of mature large groves. This can be achieved by combinations of repellents, attractants, immune enhancement promoters, mating disruption, reproduction interference, etc. Furthermore, this is accomplished by the following strategy: the first distributed system (pumped or gravity system) is situated at the perimeter or border to release a repellent compound for the purpose of repelling or keeping pests from entering the grove. The second distributed system is located within the interior of the grove and dispenses an attractant compound that attracts beneficial insects or organisms, or attracts psyllids to a trapping or killing site and/or assists in the promotion of inducing resistance that helps plants resist and recover from diseases. Thus, there can be any combination of manually replenished methods and systems and distributed methods and systems or any combination of distributed methods and systems to accomplish any desired combined purposes of protection, enhancement, etc.

Field tests were performed using a single citrus tree (6 feet high and 4 feet wide) that was heavily infested with psyllids and infected with HLB disease located in a non-pesticide sprayed urban area near Naples, Fla. It was observed that the citrus tree was flushing, then a tap test was performed and significant psyllids were confirmed to be present. A manually replenished system was installed using a volatile compound. Weekly tap tests and visual inspection using a magnifying glass confirmed that the volatile compound did not repel the psyllids. However, a different volatile compound was selected, and the test continued. Initial tap test and visual inspection revealed that the tree was heavily infested, and weekly evaluations confirmed that this volatile also was not repelling the psyllids. Another different volatile compound was selected, and the test continued. Weekly tests and observations showed that while this volatile compound did not completely eliminate the psyllids, it was observed that the test count was reduced by more than an order of magnitude. Thereafter, a different volatile blend was selected. Tap tests and observation showed that the tree was still infested, but at a lower level than when the tests initially commenced. Significantly, however, tap tests reflected the same level of adult psyllid infestation, but magnified visual observation showed no eggs or nymphs present. Weekly tests and observations continued with the resulting find of zero to 3 adult psyllids on all occasions and only one nymph on two occasions. The average release rate of the selected volatile from the system was 83 mg/day during this test. From these tests it was concluded that using the manually replenished system this volatile blend can be effective in dramatically reducing the adult population of psyllids on a small tree that had been heavily infested initially. This last test continued through two flush periods. Additionally during a five month period only one nymph was found on two occasions, reflecting a very favorable impact on reducing the reproduction of psyllids.

It should be noted that nearby the test tree there was an untreated citrus tree (comparative standard) that was also heavily infested with psyllids and continued to be heavily infested with adults, prolific eggs and nymphs during three flush periods experienced during these tests. The presence of this untreated tree and the observed conditions each week confirm the validity of the results observed on the treated test tree. Clearly, the manually replenished method and system are effective when using an appropriate/correct volatile repellent compound(s) in a single tree application. This could successfully address the "back yard" trees which have presented problems in other citrus disease fighting programs in the past.

Example 4

The present invention has the potential for use in Integrated Pest Management (IPM) programs such as those to protect forest and urban trees from native and exotic pests. In the United States successful forest management is not possible without trapping programs capable of detecting low-density populations of target species. The present invention holds excellent promise as a replacement method for the currently used bait dispersion methods employed in insect monitor trapping and tree protection.

The southern pine beetle has caused unprecedented losses to southern pine trees in recent years. Forestry management programs use various synthetic pheromones and terpenes on species being monitored as a sampling tool. A more effective trapping method based on chemical lure dispersal is economically important for protecting both the forests and urban trees from native pests and exotic invaders. In practice, each trap is baited with a conventional lure (e.g., turpentine/ethanol, SPB-Sirex lure, frontalin lure). Typically, chemical lures are often replaced biweekly to restore their effectiveness in the field. The present invention should reduce the economic cost by greatly decreasing the frequency of lure replacement as well as providing a more constant dispersal rate of application.

The present invention is undergoing field trials in the southern pine beetle-monitoring program. The chemicals that can be employed in the present invention for forestry and urban tree applications include lures such as frontalin, turpentine, ethanol, alpha-pinene, verbonone, as well as the repellent 4-allyl anisole, but are not limited to these chemical compounds.

Example 5

The present invention can be used for control of pests and pest-borne diseases in a wide variety of practical applications ranging from the protection of agricultural products such as fruits, vegetables, trees and flowers. Among the benefits, especially when large-scale application systems are implemented, will be reduced usage of various pesticides with significant reduction in pesticide residues in crop products, thereby also yielding overall environmental and food product safety benefits.

The potato industry has a parallel threat similar to that of the citrus industry that is spread by a similar psyllid. The impact on Irish potatoes is a discoloration in streaks such that potato chips made from these potatoes appear with streaks of discoloration called "zebra chips". The methods and systems, both manual and distributed, with the correct volatile compound(s) should be an excellent way of repelling these potato psyllids.

Another food industry that faces threats from insects and insect-vectored diseases is the avocado industry. Using the manual and distributed methods and systems to disperse the correct volatile compound(s) should give this industry a new tool to fight the threat caused by insects and insect vector-borne diseases.

Disclosed herein, then, are methods and systems that can function as manually replenished or distributed, the latter can cover wider areas and more objects to be treated/protected/etc. Distributed can be pumped or gravity-fed. The flow rate is extremely low in both cases. In this regard, the pipes delivering the volatile compound to the nozzles can be considered to be part of the compound-storing structures as well, given the extremely low flow rates.

While the invention has been described with reference to preferred and example embodiments, it will be understood by those skilled in the art that a variety of modifications, additions and deletions are within the scope of the invention, as defined by the following claims.

The invention claimed is:

1. A method for multiple specific applications to create and maintain pre-designed geometrically shaped volumes of an effective dynamic mixture of volatile compounds in a vapor state for very long times, up to one or more years, to control harmful pests impacting beneficial plants, domestic animals and humans, an object of protection, in open outdoor environments, the method comprising the steps of:

analyzing requirements of a selected specific application of the multiple specific applications, the requirements including pest species, site environment, site topography and the object of protection;

designing a vapor delivery system to accomplish a desired protection for the selected specific application;

selecting system components and applicable volatile compounds to accomplish the desired protection for the selected specific application;

fabricating passive flow control nozzles capable of delivering specified release rates of the volatile compounds in the vapor state for the selected specific application;

assembling volatile compound-storing structures with replenishing connectors attached to the passive flow control nozzles, the volatile compound-storing structures configured for containing a volatile compound in a liquid state therein;

positioning a plurality of the passive flow control nozzles with the specified release rates in predetermined strategic locations and unique orientations to create and maintain the pre-designed geometrically shaped volumes of volatile compounds encompassing the object of protection;

constructing on site the vapor delivery system as designed;

filling the volatile compound-storing structures with the volatile compound in the liquid state, the volatile compound-storing structures connected to the passive flow control nozzles, the passive flow control nozzles preventing the volatile compound from passing therethrough in the liquid state but permitting emission of the volatile compound in a vapor state out of the compound-storing structure and into the pre-designed geometrically shaped vapor volume;

installing a system component to protect a mass-regulating barrier from external contamination during operation;

initiating start up of the vapor delivery system for operation, and delivering the volatile compounds in the vapor state from the passive flow control nozzles at the specified release rates for the selected specific application;

monitoring that concentrations of volatile compounds in the vapor state are adequate within the pre-designed geometrically shaped volumes encompassing the object of protection;

monitoring that biologically effective thresholds are achieved within the pre-designed geometrically shaped volumes of volatile compounds in the vapor state encompassing the object of protection;

adjusting the vapor delivery system to obtain optimum performance throughout a planned protection period; and inspecting, refilling, cleaning, repairing and maintaining the vapor delivery system as needed.

2. The method of claim 1, wherein release of volatile compounds in the vapor state is into an open local environment.

3. The method of claim 1, wherein release of volatile compounds in the vapor state is into an open field environment.

4. The method of claim 1, wherein the volatile compounds comprise pest repellents.

5. The method of claim 1, wherein the volatile compounds comprise naturally-occurring pest repellents.

6. The method of claim 1, wherein the volatile compounds comprise pest attractants.

7. The method of claim 1, wherein the volatile compounds comprise naturally-occurring pest attractants.

8. The method of claim 1, wherein the volatile compounds comprise attractants for attracting beneficial insects for biological control.

9. The method of claim 1, wherein the volatile compounds comprise naturally-occurring attractants for attracting beneficial insects for biological control.

10. The method of claim 1, wherein the volatile compounds comprise pesticides.

11. The method of claim 1, wherein the volatile compounds comprise naturally-occurring pesticides.

12. The method of claim 1, wherein the volatile compounds comprise pheromones.

13. The method of claim 1, wherein the volatile compounds comprise constituents that provide enhanced plant immune responses.

14. The method of claim 1, wherein the volatile compounds comprise constituents that provide mating disruption of pests.

15. The method of claim 1, wherein the volatile compounds comprise constituents that provide interference with sexual reproduction of pests.

16. The method of claim 1, wherein the volatile compounds in the vapor state are effective in protecting plants.

17. The method of claim 1, wherein the volatile compounds in the vapor state are effective in repelling or killing mosquitoes, flies, ticks, midges and other pests.

18. The method of claim 1, wherein the volatile compounds in the vapor state are effective in integrated pest management programs.

19. The method of claim 1, wherein the volatile compounds in the vapor state are effective for protection of plants and foodstuffs in storage.

20. The method of claim 1, wherein the volatile compounds in the vapor state are effective for protection of plants and foodstuffs in transit.

21. The method of claim 1, wherein the volatile compounds in the vapor state are effective for enhanced biological control such as push-pull strategies that use both repellents and attractants.

* * * * *